(12) United States Patent
Gelfand et al.

(10) Patent No.: US 6,689,083 B1
(45) Date of Patent: Feb. 10, 2004

(54) CONTROLLER FOR ULTRAFILTRATION BLOOD CIRCUIT WHICH PREVENTS HYPOTENSION BY MONITORING OSMOTIC PRESSURE IN BLOOD

(75) Inventors: Mark Gelfand, New York, NY (US); John J. O'Mahony, Hackensack, NJ (US); Howard R. Levin, Teaneck, NJ (US)

(73) Assignee: CHF Solutions, Inc., New York, NY (US)

( * ) Notice: Subject to any disclaimer, the term of this patent is extended or adjusted under 35 U.S.C. 154(b) by 40 days.

(21) Appl. No.: 09/721,778

(22) Filed: Nov. 27, 2000

(51) Int. Cl.[7] .......................... A61M 37/00; C02F 1/44; C02F 1/00

(52) U.S. Cl. ..................... 604/5.04; 604/6.09; 210/741; 210/645; 210/647

(58) Field of Search ................................. 210/645–647, 210/741, 739, 90; 604/5.01, 5.04, 6.09, 6.11

(56) References Cited

U.S. PATENT DOCUMENTS

| | | | |
|---|---|---|---|
| 4,080,958 A | | 3/1978 | Bregman et al. |
| 4,086,924 A | | 5/1978 | Latham, Jr. |
| 4,202,764 A | * | 5/1980 | Afflerbaugh et al. ... 210/321.65 |
| 4,657,529 A | | 4/1987 | Prince et al. |
| 4,936,980 A | | 6/1990 | Yoshimichi et al. |
| 5,114,580 A | | 5/1992 | Ahmad et al. |
| 5,312,550 A | | 5/1994 | Hester |
| 5,431,811 A | * | 7/1995 | Tusini et al. ................ 210/117 |
| 5,476,451 A | | 12/1995 | Ensminger et al. |
| 5,536,237 A | | 7/1996 | Prince et al. |
| 5,589,077 A | * | 12/1996 | Matsuda et al. ............. 134/902 |
| 5,660,722 A | * | 8/1997 | Nederlof ................. 210/321.65 |
| 5,685,989 A | | 11/1997 | Krivitski et al. |
| 5,707,086 A | | 1/1998 | Treu et al. |
| 5,725,776 A | | 3/1998 | Kenley et al. |
| 5,792,367 A | * | 8/1998 | Mattisson et al. ........... 210/646 |
| 5,906,589 A | | 5/1999 | Gordon et al. |
| 5,910,252 A | | 6/1999 | Truitt et al. |
| 5,947,689 A | * | 9/1999 | Schick .................... 210/195.2 |
| 6,090,048 A | | 7/2000 | Hertz et al. |
| 2002/0068015 A1 | | 6/2002 | Polaschegg et al. |

FOREIGN PATENT DOCUMENTS

| | | |
|---|---|---|
| DE | 26 44 062 | 9/1976 |
| WO | WO 97/15228 | 5/1997 |

OTHER PUBLICATIONS

Piergiuseppe Agostoni et al., "Sustained Improvement in Functional Capacity After Removal of Body Fluid With Isolated Ultrafiltration in Chronic Cardiac Insufficiency: Failure of Furosemide to Provide the Same Result", Mar. 1994, The American Journal of Medicine, vol. 96, pp. 191–199.

(List continued on next page.)

Primary Examiner—Angela D. Sykes
Assistant Examiner—Leslie R Deak
(74) Attorney, Agent, or Firm—Nixon & Vanderhye, P.C.

(57) ABSTRACT

A method and system for the extracorporeal treatment of blood to remove fluid from the fluid overloaded patient is disclosed that non-invasively measures osmotic pressure across a filter membrane of a blood filter. The filter is permeable to water and electrolytes, but not to blood protein. The osmotic pressure indicates the protein concentration in the blood. Osmotic pressure is used to detect when hypotension is about to occur in a patient, as a result of excessive blood volume reduction during treatment of the blood. Using the osmotic pressure measurement as a feedback signal, the rate of fluid extraction is automatically controlled to achieve the desired clinical outcome and avoid precipitating a hypotensive crisis in the patient.

28 Claims, 8 Drawing Sheets

OTHER PUBLICATIONS

Daniel Goldstein et al., "Venoarterial Shunting for the Treatment of Right Sided Circulatory Failure After Left Ventricular Assist Device Placement", ASAIO Journal 1997, pp. 171–176.

Michael Berkoben et al., "Hemodialysis Vascular Access", pp. 41–57.

Allan Lauer, "Continuous Arteriovenous Hemofiltration in the Critically Ill Patient", pp. 455–460.

A. L'Abbate et al., "Ultrafiltration: A Rational Treatment for Heart Failure", Cardiology 1989, pp. 384–390.

Yung–Chang Chen et al., "Direct Peripheral Venopuncture: Another New Choice of Temporary Vascular Access", pp. 369–377.

James Cimino et al., "Simple Venipuncture For Hemodialysis", The New England Journal of Medicine, Sep. 20, 1962, pp. 608–609.

Drukker et al., "Replacement of Renal Function by Dialysis", pp. 334–379.

Andrea Rimondini et al., "Hemofiltration as Short–Term Treatment for Refractory Congestive Heart Failure", Jul. 1987, The American Journal of Medicine, vol. 83, pp. 43–48.

Marc Silverstein et al., "Treatment of Severe Fluid Overload by Ultrafiltration", vol. 291, No. 15, Oct. 10, 1974, pp. 747–751.

Strife, C.F. et al., "Experience With a Low Volume Ultrafiltration Cell in Small Children," Clinical Nephrology 8:410–413 (1977).

Lauer, A. et al., "Continuous Arteriovenous Hemofiltration in the Critically Ill Patient, Clinical Use and Operational Characteristics," Annals of Internal Medicine 99:455–460 (1983).

Verbanck, J. et al., "Pure Ultrafiltration by Repeated Puncture of a Peripheral Arm–Vein as Treatment of Refratory Edema", The International Journal of Artificial Organs, vol. 3, No. 6, (1980), pp. 342–343.

Silverstein et al, "Treatment of Severe Fluid Overload by Ultrafiltration," The New England Journal of Medicine, vol. 291, No. 15, Oct. 10, 1974, pp. 747–751.

Blake, P. et al, "Refractory Congestive Heart Failure: Overview and Application of Extracorporeal Ultrafiltration," Critical Care Nephrology, Advances in Renal Replacement Therapy, vol. 3, No. 2 (Apr. 1966), pp. 441–446.

Jenkins, R.D. et al., "The Use of Continuous Arteriovenous Hemofiltration With Hemodialysis in a Newborn," Draft #6, Personal Communication, 1985 (6 pages).

Jacobs, C. et al, "Continuous Arteriovenous Hemofiltration," Replacement of Renal Function By Dialysis, $4^{th}$ Ed., (1996) pp. 391–397.

Gupta, B.B. et al., "High Shear Rate Hemofiltration: Influence of Fiber Dimensions and Shear Rates," Artificial Organs, International Society for Artificial Organs, vol. 13(2) (1989), pp. 97–102.

Rimondini, A. et al., "Hemofiltration as Short–Term Treatment for Refractory Congestive Heart Failure," The American Journal of Medicine, vol. 83, Jul. 1987, pp. 43–48.

Donato, L. et al, "Treatment of End–Stage Congestive Heart Failure by Extracorporeal Ultrafiltration," the American Journal of Cardiology, vol. 59, (Feb. 1, 1987), pp. 379–380.

L'Abbate, A. et al, "Ultrafiltration: A Rational Treatment for Heart Failure," Cardiology 1989; 76:384–390.

Chen, Y. et al., "Direct Peripheral Venopuncture: Another New Choice of Temporary Vascular Access" Renal Failure, 22(3), 369–377 (2000).

* cited by examiner

CONTROLLER FOR ULTRAFILTRATION BLOOD CIRCUIT WHICH PREVENTS HYPOTENSION BY MONITORING OSMOTIC PRESSURE IN BLOOD

FIELD OF INVENTION

The present invention relates to an apparatus for the extracorporal treatment of blood and more specifically to the automatic control fluid removal from the blood of patients suffering from fluid overload and averting therapy induced hypotension.

BACKGROUND OF THE INVENTION

Renal replacement therapy (RRT) has evolved from the long, slow hemodialysis treatment regime of the 1960's to a diverse set of therapy options, the vast majority of which employ high permeability membrane devices and ultrafiltration control systems.

Biologic kidneys remove metabolic waste products, other toxins, and excess water. They also maintain electrolyte balance and produce several hormones for a human or other mammalian body. An artificial kidney, also called a hemodialyzer or dialyzer, and attendant equipment and supplies are designed to replace the blood-cleansing functions of the biologic kidney. At the center of artificial kidney design is a semipermeable filter membrane that allows passage of water, electrolytes, and solute toxins to be removed from the blood. The membrane retains in the blood, the plasma proteins and other formed elements of the blood.

Over the last 15 years, the intended use of the RRT equipment the system has evolved into a subset of treatment alternatives that are tailored to individual patient needs. They include ultrafiltration, hemodialysis, hemofiltration, and hemodiafiltration, all of which are delivered in a renal care environment, as well as hemoconcentration, which is typically delivered in open heart surgery. Renal replacement therapies may be performed either intermittently or continuously, in the acute or chronic renal setting, depending on the individual patient's needs.

Ultrafiltration involves the removal of excess fluid from the patient's blood by employing a pressure gradient across a semipermeable membrane of a high permeability dialyzer. For example, removal of excess fluid occurs in hemoconcentration at the conclusion of cardiopulmonary bypass surgery. Hemodialysis involves the removal of toxins from the patient's blood by employing diffusive transport through the semipermeable membrane, and requires an electrolyte solution (dialysate) flowing on the opposite side of the membrane to create a concentration gradient. A goal of dialysis is the removal of waste, toxic substances, and/or excess water from the patients' blood. Dialysis patients require removal of excess water from their blood because they lack the ability to rid their bodies of fluid through the normal urinary function.

One of the potential risks to health associated with RRT is hypotension, which is abnormal decrease in the patient's blood pressure. An abnormally high or uncontrolled ultrafiltration rate may result in hypovolemic shock, hypotension, or both. If too much water is removed from the patient's blood, such as might occur if the ultrafiltration rate is too high or uncontrolled, the patient could suffer hypotension and/or go into hypovolemic shock. Accordingly, RRT treatments must be controlled to prevent hypotension.

Alternatively, a patient may experience fluid overload in his blood, as a result of fluid infusion therapy or hyperalimentation therapy. Certain kinds of RRT machine failures may result in fluid gain rather than fluid loss. Specifically, inverse ultrafiltration may result in unintended weight gain of a patient and is potentially hazardous. Uncontrolled infusion of fluid by whatever mechanism into the patient could result in fluid overload, with the most serious acute complication being pulmonary edema. These risks are similar in all acute and chronic renal replacement therapies (ultrafiltration, hemodialysis, hemofiltration, hemodiafiltration, hemoconcentration). Monitoring patients to detect excessive fluid loss is needed to avoid hypotension.

Rapid reduction in plasma or blood volume due to dialysis-associated ultrafiltration may cause a patient to exhibit one or more of the following symptoms: hypovolemia-hypotension, diaphoresis, cramps, nausea, or vomiting. During dialysis, plasma volume would theoretically remain constant if the plasma refilling rate equaled the UF (ultrafiltration) rate. However, refilling of the plasma is often not completed during a dialysis session. The delay in refilling the plasma can lead to insufficient blood volume in a patient.

There appears to be a "critical" blood volume value below which patients begin to have problems associated with hypovolemia (abnormally decreased blood volume). Fluid replenishing rate is the rate at which the fluid (water and electrolytes) can be recruited from tissue into the blood stream across permeable walls of capillaries. This way blood volume is maintained relatively constant. Most of patients can recruit fluid at the rate of 500 to 1000 mL/hour. When patients are ultrafiltered at a faster rate, they begin to experience symptomatic hypotension.

Hypotension is the manifestation of hypovolemia or a severe fluid misbalance. Symptomatically, hypotension may be experienced by the patient as light-headedness. To monitor patients for hypotension, non-invasive blood pressure monitors (NIBP) are commonly used during RRT. When detected early, hypotension resulting from the excessive loss of fluid is easily reversed by giving the patient intravenous fluids. Following administering fluids the RRT operator can adjust the ultrafiltration rate to make the RRT treatment less aggressive.

Ultrafiltration controllers were developed specifically to reduce the occurrence of hypotension in dialysis patients. Ultrafiltration controllers can be based on approximation from the known trans-membrane pressure (TMP), volume based or gravity based. Roller pumps and weight scales are used in the latter to meter fluids. Ultrafiltration controllers ensure the rate of fluid removal from a patient's blood is close to the fluid removal setting that was selected by the operator. However, these controllers do not always protect the patient from hypotension. For example, the operator may set the fluid removal rate too high. If the operator setting is higher than the patient's fluid replenishing rate, the operator should reduce the rate setting when the signs of hypotension manifest. If the excessive rate is not reduced, the patient may still suffer from hypotension, even while the controller operates properly.

Attempts were made during the last two decades to develop monitors that could be used for feedback control of dialysis machine parameters, such as dialysate concentration, temperature, and ultrafiltration rate and ultrafiltrate volume. Blood volume feedback signals have been proposed that are based on optical measurements of hematocrit, blood viscosity and blood conductivity. Real time control devices have been proposed that adjust the ultrafiltration rate to maintain the blood volume constant, and thereby balance the fluid removal and fluid recruitment rates. None of these proposed designs led to significant commercialization owing to the high cost of sensors, high noise to signal ratio or lack of economic incentive for manufacturers. In addition, these proposed systems required monitoring of patients by highly trained personnel.

Controllers that protect patients from hypotension are especially needed for patients suffering from fluid overload due to chronic congestive heart failure (CHF). In CHF patients, fluid overload typically is not accompanied by renal failure. In these patients mechanical solute removal is not required. Only fluid (plasma water) removal is needed. Ideal Renal Replacement Therapy (RRT) for these patients is Slow Continuous Ultrafiltration (SCUF) also known as "Ultrafiltration without Dialysis".

SCUF must be controlled to avoid inducing hypotension in the patient. Due to their poor heart condition, CHF patients are especially vulnerable to hypotension from excessively fast fluid removal. The clinical treatment objective for these patients can be formulated as: Fluid removal at the maximum rate obtainable without the risk of hypotension. This maximum rate is equivalent to fluid removal at the maximum rate at which the vascular volume can be refilled from tissue. This maximum rate for CHF patients is typically in the 100 to 1,000 mL/hour range. The rate can vary with the patient's condition and is almost impossible to predict. The rate can also change over the course of treatment, especially if the objective of treatment is to remove 2 to 10 liters of fluid.

Hypotension in CHF patients often results from a decrease of the cardiac output of the patient. Cardiac output is the volume of blood that is ejected per minute from the heart with each heart contraction. The heart pumps approximately 4–8 L/min in the normal patient. Cardiac output decreases because a heart failure patient in the heart has a reduced filling pressure. Filling pressure is the blood pressure in the right atrium of the heart. This pressure is approximately equal to the patient's venous pressure measured elsewhere in a great vein and corrected for gravity. In a fluid overloaded CHF patient Central Venous Pressure (CVP) is typically between 10 and 20 mmHg. If this pressure drops by 5 to 10 mmHg, the patient is likely to become hypotensive within minutes.

The danger of hypotension in dialysis has been recognized. U.S. Pat. No. 5,346,472 describes a control system to prevent hypotension that automatically adjusts the sodium concentration added to the dialysate by infusing a hypertonic or isotonic saline solution in response to operator input or patient's request based on symptoms. European patent EU 0311709 to Levin and Zasuwa describes automatic ultrafiltration feedback based on arterial blood pressure and heart rate. U.S. Pat. No. 4,710,164 describes an automatic ultrafiltration feedback device based on arterial blood pressure and heart rate. U.S. Pat. No. 4,466,804 describes an extracorporeal circulation system with a blood oxygenator that manipulates the withdrawal of blood to maintain CVP constant. U.S. Pat. No. 5,938,938 describes an automatic dialysis machine that controls ultrafiltration rate based on weight loss or the calculated blood volume change.

Other devices have been proposed that use arterial pressure as a feedback to the ultrafiltration controller to avoid hypotension. Automatic Non-Invasive Blood Pressure (NIBP) monitor feedback was used as a control system input. NIBP measures systolic and diastolic arterial blood pressure by periodically inflating a blood pressure cuff around the patient's arm or leg. Acoustic or oscillatory methods detect the pressure level at which blood vessels collapse. This level approximates systemic arterial blood pressure. Closed loop dialysis or fluid removal devices designed around this principle have several inherent deficiencies, including:

a) NIBP is inaccurate. Errors of up to 20 mmHg can be expected in the system. To avoid system oscillations and false alarms, the feedback would have to be slow and heavily filtered.

b) NIBP is not continuous, but is rather based on periodic pressure measurements. If the blood pressure cuff were inflated more frequently, less than every 15 minutes a patient would experience significant discomfort. Also, blood vessels change their elasticity from the frequent compressions of the blood cuff. This change in elasticity can add to the inaccuracy of cuff pressure measurements.

c) The arterial pressure in CHF patient does not drop immediately following the reduction of cardiac output. It may take considerable time for a CHF patient to exhaust their cardiac reserve. By that time, the hypotension would have already occurred and its reversal would require medical intervention. Accordingly, hypotension may occur before NIBP detects it.

d) In a CHF patient, arterial blood pressure is maintained by the body to protect the brain. Neurohormonal signals are sent in response to baroreceptors that cause vasoconstriction of blood vessels to legs, intestine and kidneys. By sacrificing other body organs, arterial blood pressure to the brain can be kept constant at the expense of reduced blood flow to organs while the cardiac output is reduced dramatically. Altogether, hypotension in a CHF patient can create a dangerous situation when the arterial blood pressure is apparently normal, while the overall condition of the patient is worsening. By the time the NIBP measurement has detected hypotension, serious medical intervention may be needed.

It is desired to have a feedback based control system that will continuously and automatically manipulate the ultrafiltration rate to achieve optimal ultrafiltration. In such a system, fluid is removed rapidly and without the risk of hypotension.

SUMMARY OF INVENTION

A method and system has been developed for removing fluid from a fluid overloaded patient at a maximum safe rate that does not require human monitoring and interaction. The system uses an osmostic pressure in a blood filter as being indicative of conditions that cause hypotension. By monitoring osmotic pressure, the system to detect the onset of hypotension and maintains a safe level of filtration rate by reducing or periodically turning off ultrafiltration. Using the system, hypotension is averted before it occurs.

A feedback system for controlling an extracorporeal blood circuit has been developed that:

a) Allows optimal rate of fluid removal in vulnerable patients by automatically measuring and monitoring various selected physiological parameters, in particularly, blood pressure and osmotic pressure.

b) Prevents episodes of hypotension so that treatment could be conducted under minimal supervision.

c) Uses robust and inexpensive measurement system.

BRIEF DESCRIPTION OF THE DRAWINGS

The attached drawings and associated written description disclose an exemplary embodiment of the present invention.

DETAILED DESCRIPTION OF PREFERRED EMBODIMENTS

Figure 1:
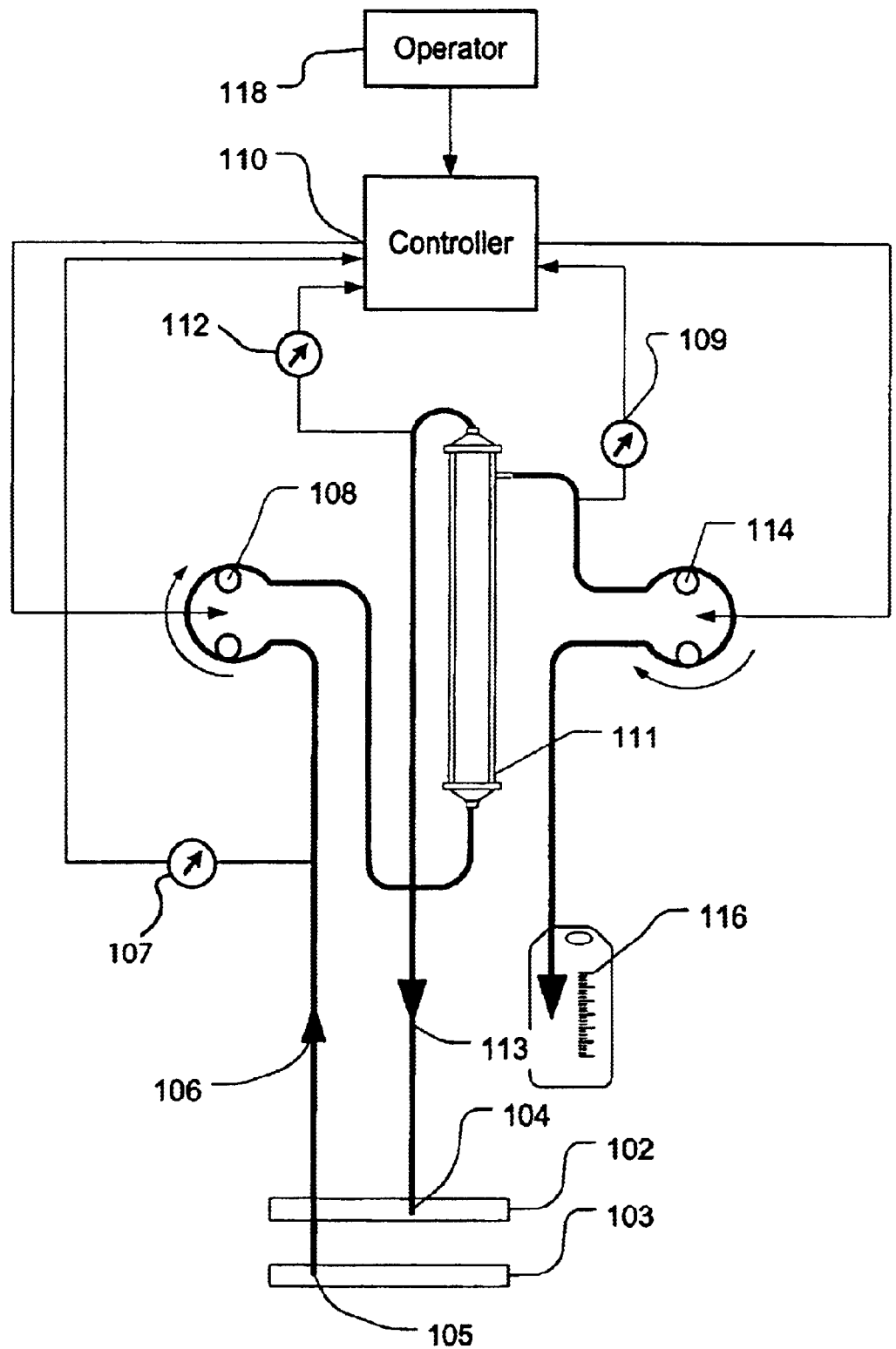
FIG. 1 shows a high level schematic diagram of an ultrafiltration system.

FIG. 1 shows a high level schematic diagram of an ultrafiltration system, such as is disclosed in commonly-owned (U.S. patent application Ser. No. 09/660,195, filed Sep. 12, 2000), entitled "Blood Pump Having A Disposable Blood Passage Cartridge With Integrated Pressure Sensor", and U.S. Pat. No. 6,585,675(U.S. patent application Ser. No. 09/703,702, filed Sep. 12, 2000), entitled "Method And Apparatus For Blood Withdrawal And Infusion Using A Pressure Controller" and filed Nov. 2, 2000, both of which applications are incorporated by reference in their entirety.

Blood is withdrawn from the vein 103 of a human or other mammalian patient using a withdrawal needle 105. The blood flows from the needle into a withdrawal bloodline 106 that is equipped with an in-line pressure sensor 107. The sensor transmits a signal indicative of the blood pressure in the withdrawal line to a computer controller 110. The withdrawal line loops through a blood pump 108. The pump creates a suction (negative) pressure in the withdrawal line that draws blood from the vein and into the line.

The pump also forces blood through a filter 111 that removes excess fluid from the blood. The filter includes a blood passage coupled between a blood inlet and outlet to the filter, a filtering membrane forming a portion of the walls of the passage, and a filtered fluid outlet section on a opposite side of the membrane from the blood passage. The membrane is pervious to fluids, but not to blood plasma and other solutes in the blood. The filter membrane may be an artificial lipid bilayer, a plasma membrane or a layer of cells.

Some fluids (but not all) in the blood flowing through the blood passage in the filter may pass through the membrane to the outlet section and thereby be filtered from the blood. However, the plasma and solutes in the blood cannot pass through the filter membrane and remain in the blood as it exits the filter. The filter has a blood outlet connected to a return line 113 through which flows blood to be infused back into a vein 102 of the patient. The filter has a second output through which flows separated ultrafiltrate (plasma water) that passes in a filtrate line that loops through a metering pump 114 and into a collection bag 116.

The ultrafiltrate pump 114 is capable of generating a negative pressure in the filtrate line (and hence output side of the filter membrane) to assist the flux of ultrafiltrate across the membrane, which has a substantial hydraulic resistance. The pressure level in the filtrate line and in the filtrate output section of the filter is determined by the rotational speed of the ultrafiltrate pump 114. The rotational speed of pumps 108 and 114 is determined by a controller 110 that can be a microcomputer. The controller receives pressure measurements from blood line return sensor 112 and the ultrafiltrate pump sensor 109. The controller is programmed to adjust the ultrafiltrate pump speed to provide a pressure level in the filtrate line to achieve a desired filtration rate.

Generally, just prior to the ultrafiltration treatment, an operator, such as a nurse or medical technician, selects certain control settings on the controller for the treatment. The settings (which may be selected by the operator or preprogrammed into the controller, or a combination of both) may include (among other settings) a desired fluid removal rate from the blood. This rate may be applied by the controller to determine the rotational speed of the ultrafiltration pump 114.

The rotational speed of the pump 114 controls the pressure (measured by ultrafiltrate sensor 109) in the output section of the filter. The fluid pressure in the output section is present on one side of the filter membrane. The fluid pressure of the blood in the blood passage is present on the other side of the membrane. The filtration rate is dependent on the pressure difference across the membrane of the filter. The filtration rate is controlled by the pressure in the filtrate outlet section of the filter, assuming that the blood pressure in the filter blood pressure remains constant. Accordingly, the filtration rate is controlled by the speed of the ultrafiltration pump 114 which determines the fluid pressure in the filter outlet section.

The filtrate pressure sensor 109 provides a feed back signal to the controller as to the fluid pressure in the outlet section of the filter. Alternative techniques to control the filtration rate are for the controller to adjust the blood pressure in the filter passage, or to adjust both the blood pressure in the filter and the fluid pressure in the outlet section of the filter.

A safety feature of the controller is that it adjusts the filtration rate to avoid hypotension of the patient. If too much fluid is removed too rapidly from the blood of the patient, the patient may suffer from hypotension. The osmotic pressure across the filter membrane provides a good indicator of the blood volume and the osmotic pressure may be determined based on the pressure signal of the filtrate pressure sensor 109 (and, if needed, based on a comparative blood pressure signal from sensor 112 or a differential pressure sensor used between two points).

Figure 2:
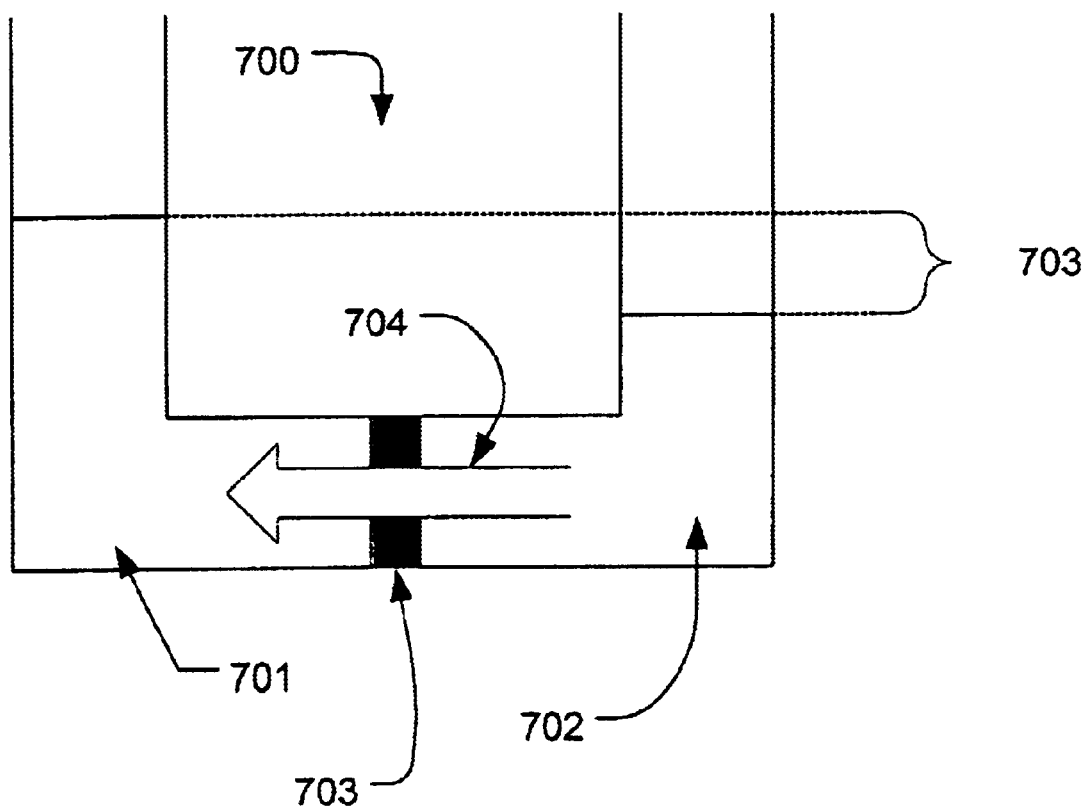
FIG. 2 illustrates relationship between hydrostatic and osmotic pressure forces.

Osmotic pressure can be used to determine the protein concentration in blood and, in turn, applied to detect hypotension in a patient. The osmotic pressure level across the filtering membrane of a blood filter is determined by difference in concentration of soluble substance (As illustrated by FIG. 2). If two solutions (e.g., blood and a filtrate removed from the blood) of different concentration are separated by a semi-permeable membrane which is permeable to the smaller solvent molecules but not to the larger solute molecules, then the solvent will tend to diffuse across the membrane from the less concentrated to the more concentrated solution. This process is called osmosis. Osmosis is a selective diffusion process driven by the internal energy of the solvent molecules. It is convenient to express the available energy per unit volume in terms of "osmotic pressure". It is customary to express this tendency toward solvent transport in pressure units relative to the pure solvent. If pure water were on both sides of the membrane, the osmotic pressure would be zero. But if normal human blood were on the right side of the membrane and pure water on another, the osmotic pressure would be about seven atmospheres.

Osmotic pressure may be measured by determining the amount of hydrostatic pressure necessary to prevent fluid transfer by osmosis (703 on FIG. 2). The flow of water across a membrane in response to differing concentrations of solutes on either side—osmosis—generates a pressure across the membrane called osmotic pressure. Osmotic pressure is the hydrostatic pressure required to stop the flow of water and is equivalent to hydrostatic pressures.

The operator enters into the controller a desired level of osmotic pressure to be present across the membrane of the filter 111. By properly selection the osmotic pressure level, the operator can prevent excessive reduction of blood volume in the patient and ensure safety from hypotension. The controller monitors the blood and filtrate pressure signals from sensors 107 and 109 (and, if present, from pressure sensors embedded in the filter and at the blood passage outlet 112 of the filter). The microprocessor controller (see FIG. 9) includes algorithms to control the ultrafiltration rate automatically based on the changes of osmotic pressure and the settings entered by the operator and preprogrammed into the controller.

The principles of osmosis and osmotic pressure are illustrated by the FIG. 2. The test apparatus 700 consists of two vessels separated by a selectively permeable membrane 703. In the left side of the apparatus is a solution 701 having a solute and a solvent. Water (a solvent) freely travels through the membrane into the right side vessel 702. The pores of the membrane prevent molecules of the solute from the blood solution 701 from crossing through the membrane from left to right into the outlet section. When the system is in steady state, the blood solution in the left container will rise so the pressure head (weight of the water column) 703 is equal to the osmotic pressure generated by the concentration difference.

The osmotic pressure P of a dilute solution is approximated by the following equation known as Hoff's equation for ionized solutions:

$$P = i \frac{C}{M} RT \qquad \text{(Equation 1)}$$

C=concentration of solute in g/L (grams per liter)
M=molecular weight of the solute
I=number of ions for ionized solutions
T=temperature of solution in the absolute scale or Kelvin
R=the gas constant (0.82 liter-atmosphere/degree-mole)

Osmotic pressure plays an important role in the design of a dialyzer or hemofilter. If no dialysis is performed (e.g., no dialysate is passed through the filter and across the separator membrane), then only the naturally occurring blood components play role in determining the osmotic pressure gradient.

Figure 3:
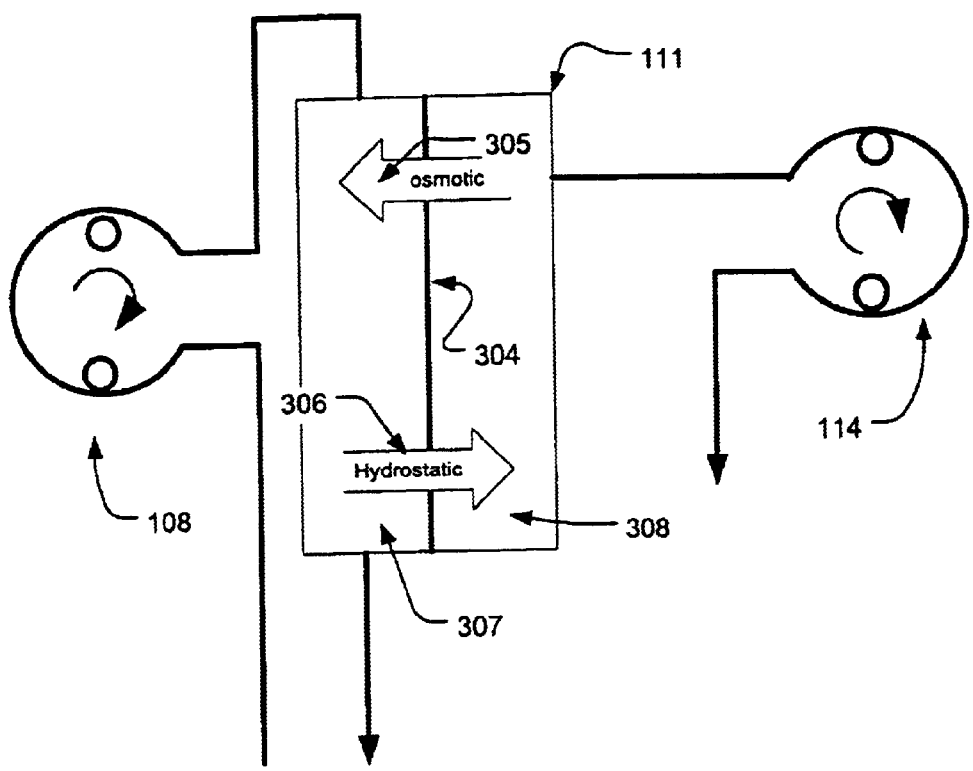
FIG. 3 shows osmotic and hydrostatic pressures across the hemofilter filter membrane with pumps running.
Figure 4:
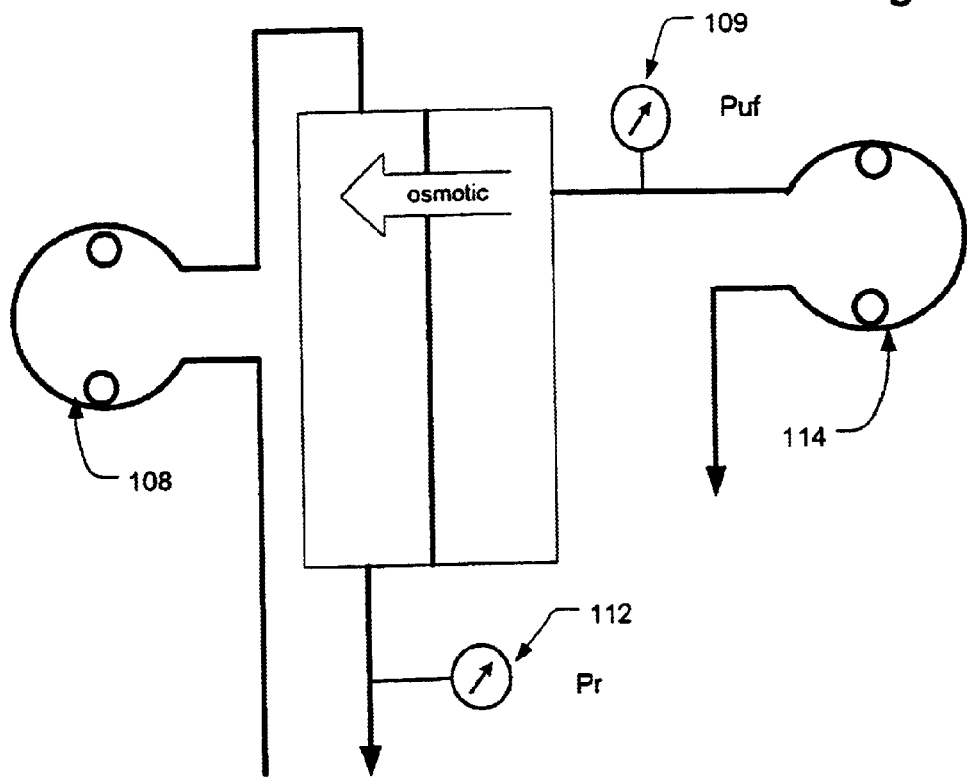
FIG. 4 shows osmotic and hydrostatic pressures across the filter membrane with pumps stopped.

FIGS. 3 and 4 show filter 111 of an ultrafiltration device having a filter membrane 304. In the filter, the blood flows through the blood passage of the filter (most often hollow fibers with permeable walls). The fluid on the outside of the filter membrane is referred to as ultrafiltrate or "plasma water". In the blood flowing through the blood passage, blood cells constitute 25 to 45% of the total blood volume.

The blood hematocrit is the percentage of the total blood volume constituted by blood cells. Blood cells themselves do not affect the osmotic pressure gradient across the filter membrane. Other than the cells, the rest of the blood volume is plasma. Plasma is an aqueous solution of electrolytes such as NaCl and proteins. Water represents about 90% of the volume in blood plasma. Water travels freely across the hemofilter filter membrane between the blood passage and output section compartments of the filter.

Ions of NaCl and other electrolytes account for about 1% of plasma. A number of 9 g/L is a typical concentration of dissolved minerals in human blood. NaCl has molecular weight of 58.44 g/mole. From the Equation 1 it can be calculated that if the filter membrane was not permeable to electrolytes (e.g., all the NaCl would be trapped on the blood passage side of the filter) the osmotic pressure generated by the relatively small (1%) concentration of NaCl will generate sufficient head to support a water column roughly 74 meters high. In clinical ultrafiltration, blood filter membranes allow free convective transport of electrolytes. As a result, concentration of NaCl on both sides of the membrane is exactly the same and it does not contribute to osmotic pressure gradient.

Soluble plasma proteins are almost fully retained by the hemofilter membrane and trapped on the blood side of the filter (e.g. inside fibers). Most significant blood protein is albumin. For simplicity further calculations will assume that albumin is the only protein retained by the membrane. Albumin molecules are much larger than ions of electrolytes but are small enough to generate significant, and more importantly measurable, amount of osmotic pressure.

To illustrate the effects of a change in the concentration of protein on osmotic pressure, the osmotic pressure was determined for separation of blood by a membrane impermeable to protein but permeable to electrolytes. A standard hemofiltration fiber such as fibers manufactured by Minntech of Minnesota, was used as a membrane for the filter. Experiments were done using bovine blood with the protein concentration adjusted to 60 g/L, which is consistent with normal physiologic conditions in human blood. Substitution of M=66,000 g/mole for albumin into Equation 1, gives an osmotic pressure of 17 mmHg after multiplying by 760 to convert pressure from atmospheres to mmHg. The experiments used bovine blood with an initial hematocrit of 27%, such that the initial volume of blood cells was 27% and the volume of plasma with solutes accounted for the remaining 73% of the plasma volume. Out of this 73% solute volume, the protein at 60 g/L of plasma accounted for 4.4% of the total volume of blood. The remaining volume was assumed to be water and small molecules that freely permeated across the filter membrane.

During the experiment, blood was condensed by filtering out plasma water with small solutes. The filter included a standard hemofiltration fiber membrane manufactured by Minntech of Minnesota. The filter membrane was formed by 900 fibers arranged in parallel and assembled into a bundle packed into the filter. Each fiber had internal diameter of 0.2 mm. This type hollow fiber filter membrane is commonly used in hemofilters, dialyzers and hemoconcentrators manufactured by many companies. During the experiment, blood was gradually condensed from hematocrit of 27% to hematocrit of 40% by extracting water through the filter membrane. The hematocrit was measured using standard lab equipment and confirmed by the removed volume fraction measurement. Since the membrane was impermeable to proteins, the protein concentration in blood increased in proportion to the hematocrit. The concentration of small molecules and minerals in the blood did not change as the blood passed through the filter.

FIGS. 3 and 4 show how the osmotic pressure can be determined in a practical apparatus (See FIG. 1). The hemofilter 111 includes a membrane 304 that is permeable to water and small molecules. Blood is pumped by the pump 108 continuously through the blood side 307 of the filter and passes over the membrane. On an opposite side of the membrane, the ultrafiltrate 308 is collected in an outlet section of the filter. The protein in the blood does not pass through the filter to the ultrafiltrate side of the filter. The pump 114 is rotated at a predetermined rate to remove water from blood. Blood is condensed as it passes through the filter. Typically 5 to 20% of water can be removed from the blood volume.

While the system is in operation, it is difficult to measure the osmotic force. The system is in the dynamic equilibrium, and only the resulting pressures in both compartments can be measured instantaneously. The resulting pressures on the filter membrane are the function of many contributors such as the dynamic resistance of the filter to blood and ultrafiltrate. FIG. 3 shows the dynamic relationship of the hydrostatic 306 and osmotic 305 pressures across the filter membrane 304. When the system is operated, as shown on the FIG. 3, with both pumps pumping, two forces act on the water molecules in the filter. Hydrostatic forces 306 generated by the pumps urge water through the membrane from the blood into the ultrafiltrate output section. Osmotic forces 305, determined mostly by the concentration of protein in the blood compartment 307, oppose the hydrostatic force. Dynamically measuring osmotic pressures (without the influence of hydrostatic forces) is not practical while blood is flowing through the filter in this configuration of the apparatus.

To measure the osmotic pressure, the ultrafiltrate pump 114 is stopped first to exclude the effects of filtration on the properties of blood. The blood pump 108 continues to pump blood through the filter 111, for a period of time at least equal to the time needed to remove the blood trapped in the filter and refill it with the fresh patient blood. If the blood volume of the filter is 10 mL and the blood pump flow is 60 mL/min., the time for running the blood pump, after the ultrafiltrate pump is stopped, will be approximately equal to 10 seconds. While the ultrafiltrate pump is stopped, no fluids are being removed from the blood by the filter and the concentration of blood cells and protein in blood is the same in the blood passage of the filter as in the patient's veins. In addition, the average pressure in both filter compartments (blood passage and ultrafiltrate output section) of the hemofilter come to equilibrium. This average equilibrium pressure is determined by the blood flow, hydraulic resistance of the blood flow path and the osmotic pressure gradient between the two filter compartments.

Next, the blood pump 104 is stopped for a short duration of time, e.g., approximately 10 seconds, to eliminate effects of the remaining hydrostatic forces from the filter. Since the equilibrium is established via diffusion of molecules of solute across the membrane it requires certain time to establish. This period is kept as short as possible to reduce risk of blood clotting. FIG. 4 illustrates the steady state condition in the filter in which both pumps 114 and 108 are stopped. The pressure difference across the membrane (between the blood passage and the ultrafiltrate outlet sides of the membrane) as measured by the difference in pressures determined by pressure sensors 112 and 109 represents the osmotic pressure gradient across the membrane, and gravitational effects due to any height difference between the sensors. Pressure sensors 112 and 109 are shown as independent devices, but may also be implemented as a single differential pressure sensor used to measure osmotic pressure across the filter membrane. The gravitational effects can be determined based on the relative heights of the sensors 112 and 109 and the gravitational effects, once determined, can be mathematically eliminated from the pressure measurements so that the osmotic pressure can be determined.

Figure 5:
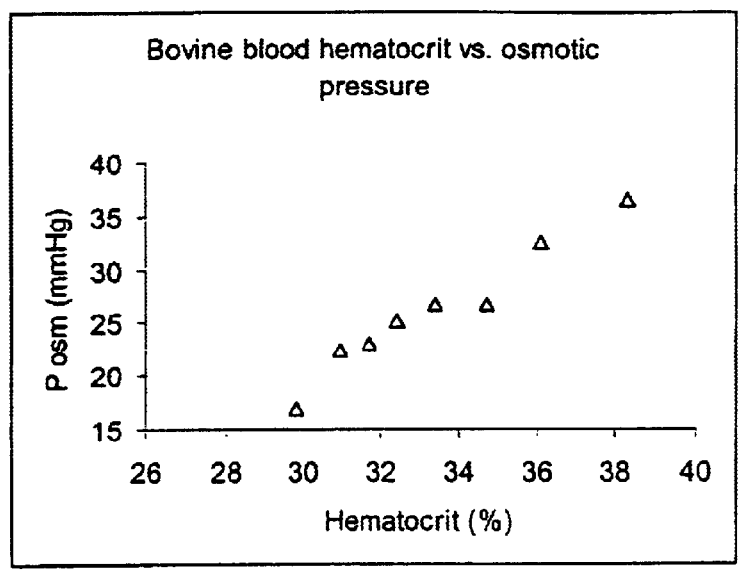
FIG. 5 shows relationship between blood hematocrit and osmotic pressure across filter membrane established in the lab.
Figure 6:
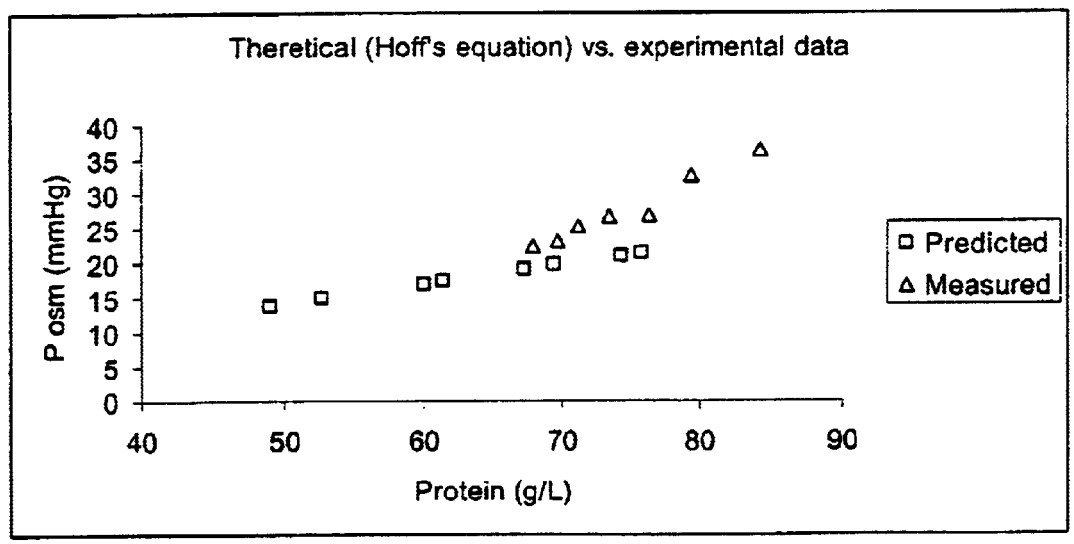
FIG. 6 shows theoretical and experimental correlation between blood protein concentration and osmotic pressure.

FIGS. 5 and 6 illustrate the results of the experiment of determining the relationship of blood hematocrit levels and the osmotic pressure across a filter membrane. FIG. 5 shows that the osmotic pressure measured across the membrane increased in linear proportion to the hematocrit level in the blood and as the water was removed from plasma. An increase of hematocrit from 29% to 38% lead to an increase of osmotic pressure from 17 to 29 mmHg. FIG. 6 shows that the results of the experiment are consistent with the theoretical prediction. The predicted values for osmotic pressure (squares) were calculated using Equation 1. Since the initial concentration of protein in blood was known, an assumption was made that the protein concentration increased ratiometrically and in inverse proportion to the removed fraction of water. The measured values (triangles) for osmotic pressure were obtained using pressure transducers connected to the blood passage and ultrafiltrate output section of the hemofilter. The experimental curve rises steeper than the theoretical results, because Hoff's equation assumes that that osmotic pressure will increase linearly with solute concentration. The experimental data shows an exponential increase in osmotic pressure. For charged molecules such as proteins, the osmotic pressure also depends on pH and the ionic strength of the solution. Experimentally derived or theoretical functions may be used to predict the concentration of protein based on measured osmotic pressure in osmotic pressure, although experimentally derived functions may be preferable.

Figure 7:
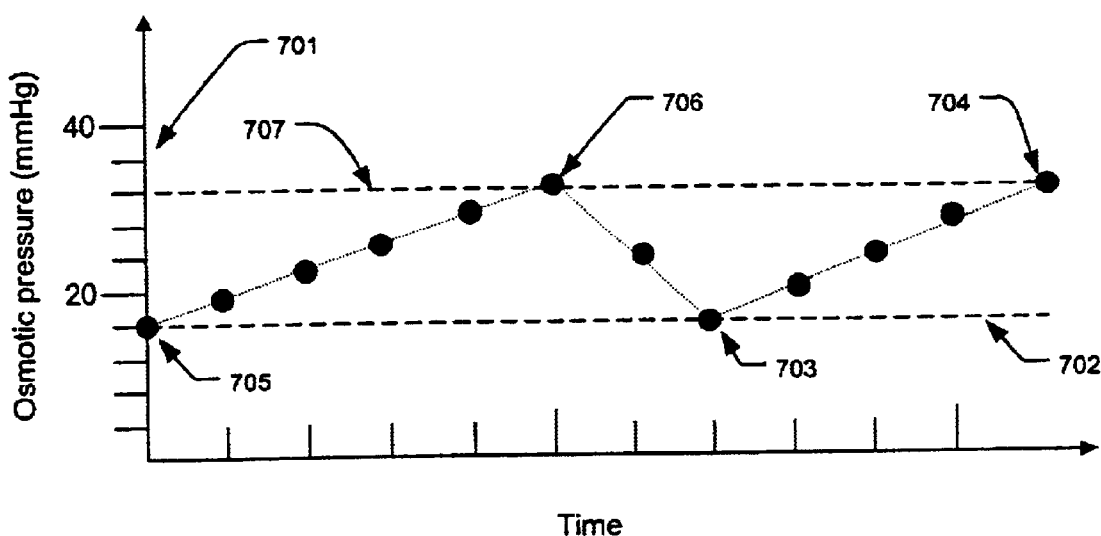
FIG. 7 illustrates a method of controlling ultrafiltration by establishing a predetermined deviation of osmotic pressure from baseline value.

FIG. 7 shows an implementation of a method, described above, to control fluid removal and prevent hypotension when using an ultrafiltration extracorporeal circuit to remove excess fluid from a patient's blood. Osmotic pressure, plotted on the Y axis 701, is periodically measured. Dots such as 703 and 704 correspond to periodic osmotic measurements over the time course of treatment. Since clinical filtration usually removes water at slow rates 500 to 1000 mL/min, measurements can be performed every 15 or 30 minutes. In this example, fluid removal rate exceeds the rate at which the blood volume can be replenished with the water stored in tissue. As a result the protein concentration and osmotic pressure across the hemofilter are gradually rising between the point 705 corresponding to the start of treatment and the point 706 when the predetermined allowed level of osmotic pressure 707 is reached. Level 707 can be set by the operator at the beginning of treatment or calculated by the machine as a function of the initial osmotic pressure level 702.

The initial osmotic pressure 702 level may be measured at the beginning of ultrafiltration treatment. The osmotic maximum pressure limit 707 may be automatically established as the initial level 702 plus a predetermined delta osmotic pressure level, for example, 20% of the initial level. When the limit level 707 is reached, the controller automatically stops the ultrafiltrate pump or reduces the rate at which the fluid is removed. The blood pump speed is not changed while the ultrafiltrate pump is slowed or stopped. Between points 706 and 703, the blood volume in the blood circuit and filter is replenished from patient's tissue. The replenishment of unfiltered blood should cause the osmotic pressure level to return to the level 702. At stage 703, the ultrafiltration rate is increased. Many other control algorithms can be implemented to control ultrafiltration rate based on the osmotic pressure across a hemofilter membrane. Existing control algorithms are well known, and may be modified to include patient safeguards based on monitoring osmotic pressure.

Figure 8:
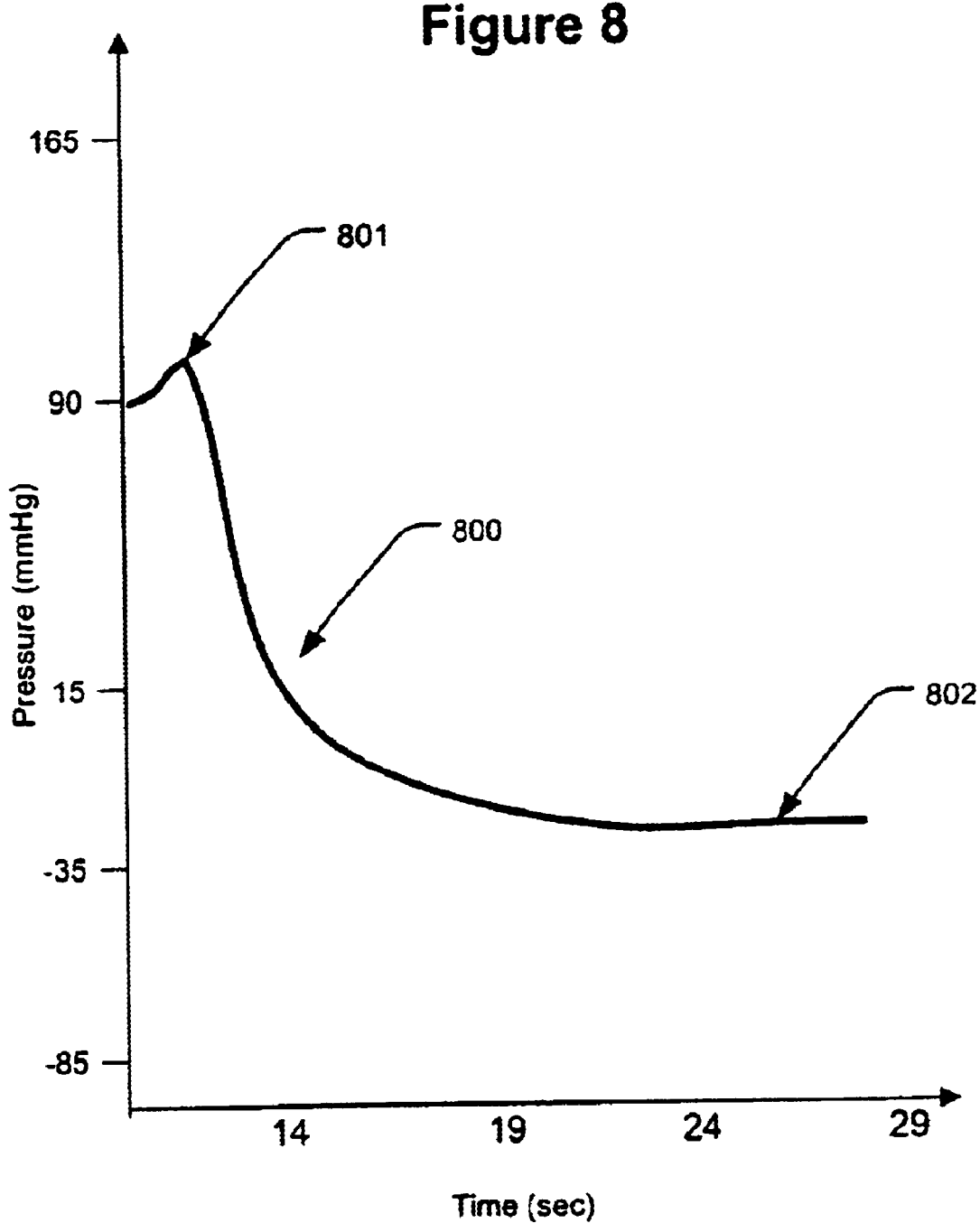
FIG. 8 shows time course of stabilization of osmotic pressure after pumps are stopped using animal blood.

FIG. 8 illustrates the transition to steady state in the system (See FIGS. 2 and 3) when both pumps are stopped. The curve was obtained experimentally with animal blood using an apparatus similar to one illustrated by FIG. 1. Curve 800 shows the change of pressure (vertical axis of chart) measured by sensor 109 on the ultrafiltrate side of the filter membrane just after the blood pump is stopped. The ultrafiltrate pump was also stopped prior to the measurement. At the beginning of the transition, before point 801, the pressure on the ultrafiltrate side of the filter membrane is positive and relatively high, at approximately 90 mmHg. Since the ultrafiltrate pump 104 is stopped, this pressure 801 is equal to the hydrostatic pressure generated by the blood flow through the resistive filter circuit minus the osmotic pressure across the membrane (referenced to the atmospheric pressure). Hydrostatic pressure will generally dominate when blood is flowing through the filter with high hydraulic resistance.

At the point 801, the blood pump is stopped and the hydrostatic pressure forces are eliminated. The pressure measured by the sensor 109 begins to drop and changes polarity. When the transition is complete, the ultrafiltrate pressure is at −15 to −40 mmHg relative to atmospheric depending on the concentration of protein in the patient's blood. As can be seen from the decay curve 800 on the FIG. 8, a steady state is reached in approximately 10 seconds after the blood pump is stopped. It is desired not to stop the flow of blood for longer than several seconds to avoid blood clots in the circuit. Delaying the filtration by stopping the filtrate pump does not raise a risk of clotting and, thus, the period during which filtration is stopped is not as time sensitive as is the period during which the blood pump is stopped. To achieve the shortest equilibration time (e.g., 10 seconds), the circuit should have minimal compliance and the filter should be fully primed and not trap air.

In determining osmotic pressure, the effects of gravity (altitude) on the measurement need to be accounted for and excluded from the calculation of osmotic pressure. The pressure generated by the weight of the fluid column can be expressed by Equation 2 below:

$$Ph = RO \times G \times H \quad \text{(Equation 2)}$$

Where RO is the density of fluid, G is the gravitational constant, and H is the height of the sensor 109 in relation to the blood access 104 in the patient's vein 102. Since blood has proximately the same density as water sudden change of the position of the patient's arm by 10 cm will result in a 7.3 mmHg shift of the Puf measured with the sensor 109.

It is assumed that the relative position of sensors 109 and 112 is known and does not change during treatment. When the system is in steady state, the readings of the sensors are described by Equations 3 below:

$$Puf = Posm + Pv + Ph \quad \text{(Equations 3)}$$
$$Pr = Pv + Ph$$

Pr=pressure measured at the machine level in the blood return line 113 with the pressure sensor 112.
Puf=pressure measured at the machine level with the sensor 109 in the ultrafiltrate line between the filter and the pump.
Pv=blood pressure in the patient's vein.
Ph=offset determined by the height difference between the machine mounted sensors and the patient blood return connection.

Equations 3 can be solved for osmotic pressure (Posm). Equation 4 can be used to dynamically calculate osmotic pressure across the filter membrane, where the pressure determination is free of the influence of the patient's position and blood pressure.

$$Posm = Puf - Pr \quad \text{(Equation 4)}$$

Figure 9:
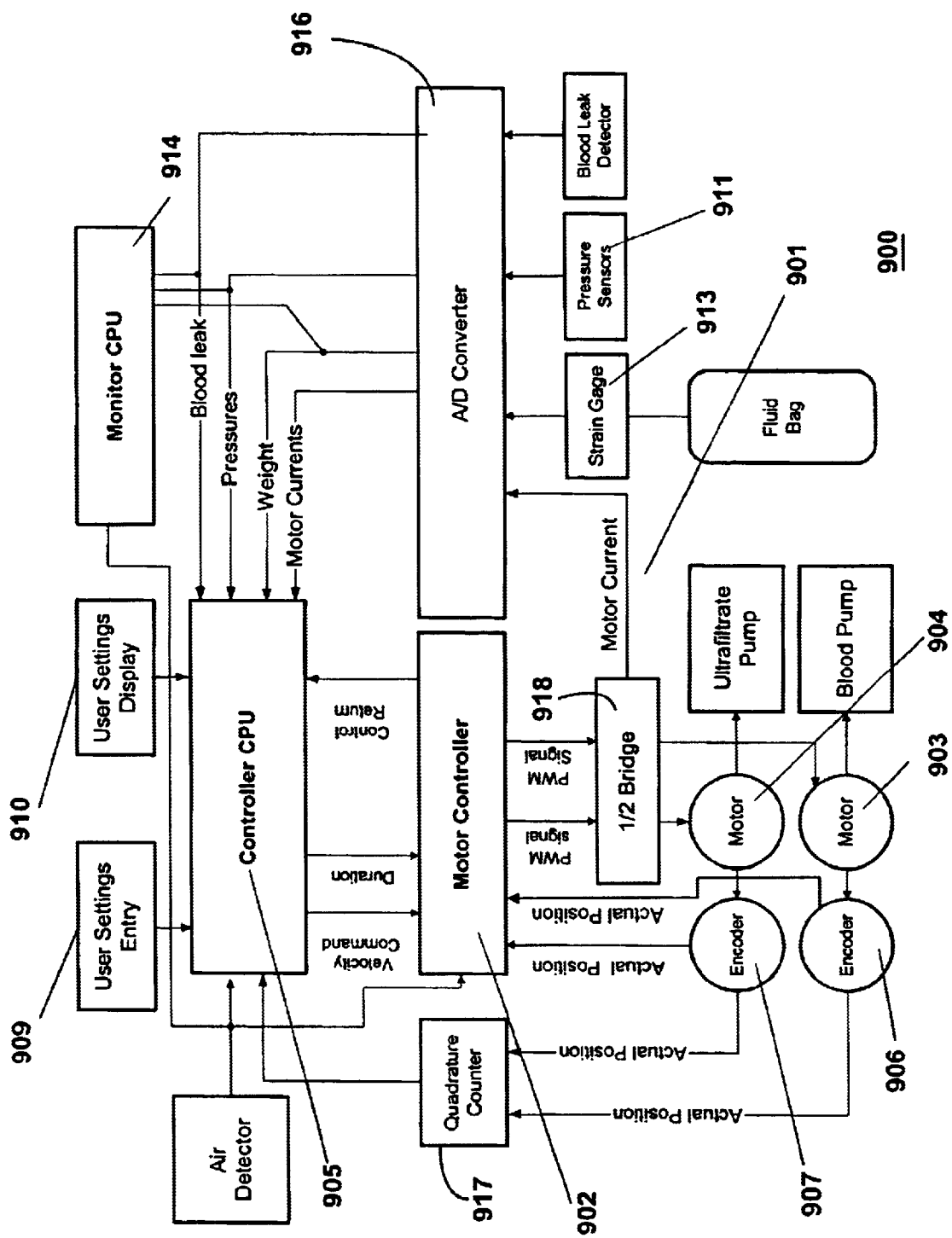
FIG. 9 illustrates design of the controller for ultrafiltration apparatus.

FIG. 9 illustrates the electrical architecture of the ultrafiltration controller system 900 (110 in FIG. 1), showing the various signal inputs and actuator outputs to the controller. The user-operator inputs the desired ultrafiltrate extraction rate into the controller by pressing buttons on a membrane interface keypad 909 on the controller. These settings may include the maximum flow rate of blood through the system, maximum time for running the circuit to filter the blood, the maximum ultrafiltrate rate and the maximum ultrafiltrate volume. The settings input by the user are stored in a memory and read and displayed by the controller CPU 905 (central processing unit, e.g., microprocessor or microcontroller) on the display 910.

The controller CPU regulates the pump speeds by commanding a motor controller 902 to set the rotational speed of the blood pump 113 to a certain speed specified by the controller CPU. Similarly, the motor controller adjusts the speed of the ultrafiltrate pump 111 in response to commands from the controller CPU and to provide a particular filtrate flow velocity specified by the controller CPU.

Feedback signals from the pressure transducer sensors 911 are converted from analog voltage levels to digital signals in an A/D converter 916. The digital pressure signals are provided to the controller CPU as feedback signals and compared to the intended pressure levels determined by the CPU. In addition, the digital pressure signals may be displayed by the monitor CPU 914.

The motor controller 902 controls the velocity, rotational speed of the blood and filtrate pump motors 903, 904. Encoders 907, 906 mounted to the rotational shaft of each of the motors as feedback provide quadrature signals (e.g., a pair of identical cyclical digital signals, but 90° out-of-phase with one another). These signal pairs are fed to a quadrature counter within the motor controller 902 to give both direction and position. The direction is determined by the signal lead of the quadrature signals. The position of the motor is determined by the accumulation of pulse edges. Actual motor velocity is computed by the motor controller as the rate of change of position. The controller calculates a position trajectory that dictates where the motor must be at a given time and the difference between the actual position and the desired position is used as feedback for the motor controller. The motor controller then modulates the percentage of the on time of the PWM signal sent to the one-half 918 bridge circuit to minimize the error. A separate quadrature counter 917 is independently read by the Controller CPU to ensure that the Motor Controller is correctly controlling the velocity of the motor. This is achieved by differentiating the change in position of the motor over time.

The monitor CPU 914 provides a safety check that independently monitors each of the critical signals, including signals indicative of blood leaks, pressures in blood circuit, weight of filtrate bag, motor currents, air in blood line detector and motor speed/position. The monitor CPU has stored in its memory safety and alarm levels for various operating conditions of the ultrafiltrate system. By comparing these allowable preset levels to the real-time operating signals, the monitoring CPU can determine whether a safety alarm should be issued, and has the ability to independently stop both motors and reset the motor controller and controller CPU if necessary.

Figure 10:
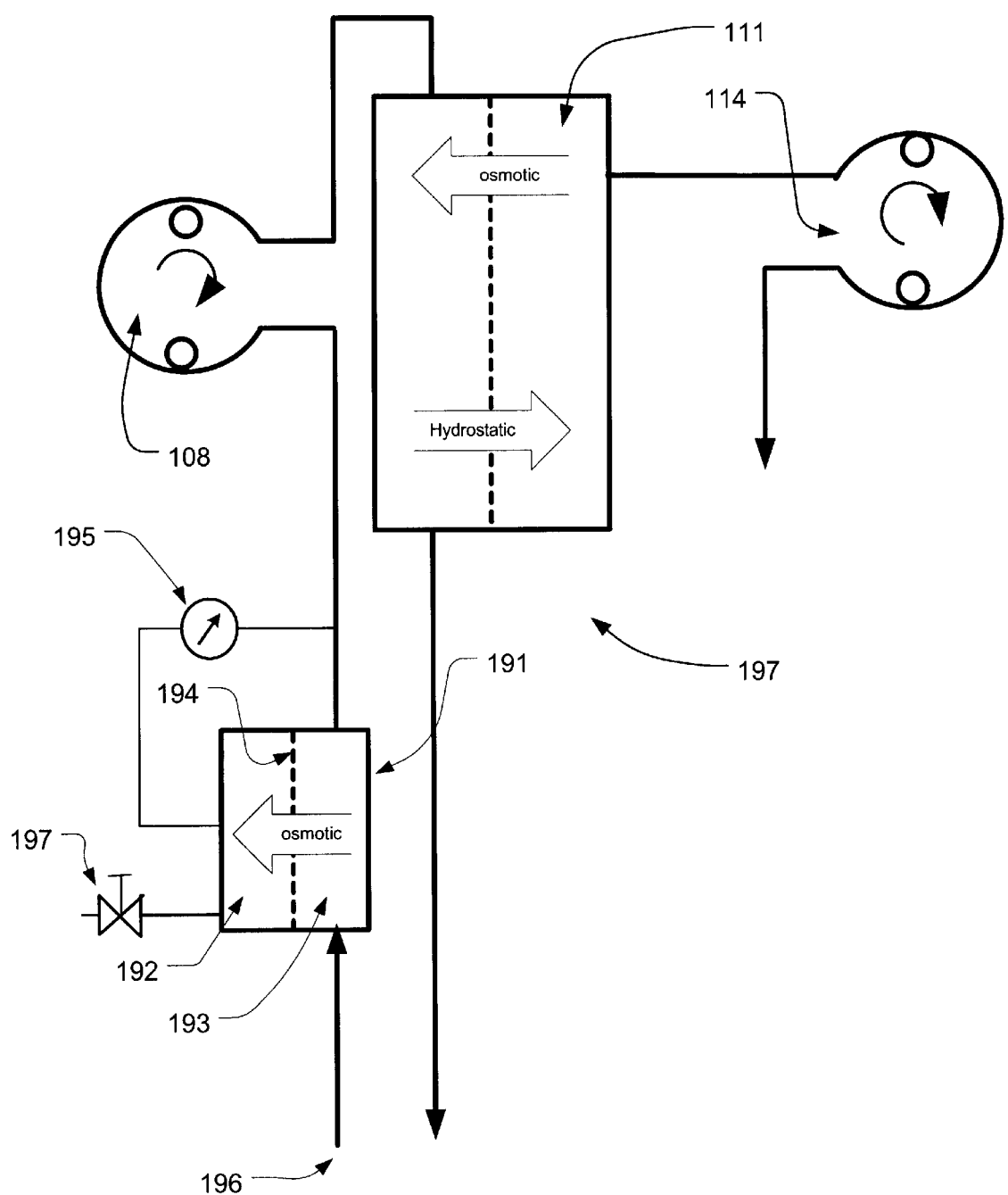
FIG. 10 shows an embodiment of the invention where osmotic pressure measurement is separate from blood filter.

FIG. 10 shows an ultrafiltration apparatus where the osmotic pressure measurement is separate from the hemofilter. The apparatus for ultrafiltration of the blood 197 is similar to the filter shown in FIGS. 3 and 4. The apparatus is equipped with a hemofilter of dialyzer 111. An ultrafiltrate or dialysate pump 114 removes plasma water, or pumps the dialysate across the filter membrane. Osmotic pressure measuring device 191 is separate from the hemofilter 111. The pressure measuring device 191 has a blood chamber 193 separated from the filtrate chamber 192 by membrane 194. The membrane 194 is permeable to water and electrolytes, but impermeable to protein and blood cells.

Blood withdrawn from the patient (not shown) travels through the withdrawal tubing 196 into the blood chamber 191, when the roller pump 108 rotates. The chamber 191 presents little hydrostatic resistance to blood flow. During priming of the circuit, the filtrate chamber 192 is filled with plasma water by applying a source of negative pressure to the port 197. When the chamber 192 is filled and free of air, the port 197 is closed. During treatment, blood from the patient flows continuously through the device 191. A differential pressure transducer 195 measures the pressure difference between the blood chamber 193 and the filtrate chamber 192 in the device 191. This pressure difference is the osmotic pressure proportional to the concentration of protein in blood. This system is insensitive to changes in hydrostatic pressure generated by blood flow or gravity since it affects both chambers equally in device 191. While the embodiment shown in FIG. 10 requires additional equipment, the embodiment can be used continuously without stopping the blood flow to measure osmotic pressure. It can also be used in applications where the filter 111 is used for hemodialysis. With the separate chamber 191, the osmotic pressure difference generated by electrolytes in the dialysis fluid passing through the filter 111 does not affect monitoring of the blood volume change.

The preferred embodiment of the invention now known to the invention has been fully described here in sufficient detail such that one of ordinary skill in the art is able to make and use the invention using no more than routine experimentation. The embodiments disclosed herein are not all of the possible embodiments of the invention. Other embodiments of the invention that are within the sprite and scope of the claims are also covered by this patent.

What is claimed is:

1. A method for preventing hypotension in a mammalian patient whose blood is being withdrawn, treated in an extracorporeal blood circuit and infused into the patient, said method comprising:
   a. withdrawing blood from the patient into the extracorporeal blood circuit, condensing the blood by removing fluid from the blood using a permeable membrane in the blood circuit, and infusing the condensed blood to the patient;
   b. monitoring an osmotic pressure by periodically stopping the blood flow and filtrate flow across the permeable membrane to measure the osmotic pressure level across the permeable membrane, and
   c. adjusting a rate of removal of the fluid from the blood and through the permeable membrane or filter if the measured osmotic pressure level varies from a predetermined osmotic pressure setting.

2. A method for preventing hypotension as in claim 1 wherein the osmotic pressure setting is a maximum osmotic pressure level.

3. A method for preventing hypotension as in claim 2 wherein the maximum osmotic pressure setting is a sum of a osmotic pressure level determined during an initial phase of treating the blood in the circuit and a predetermined delta osmotic pressure level.

4. A method for preventing hypotension as in claim 3 wherein the predetermined delta osmotic pressure level is selected by an operator.

5. A method for preventing hypotension as in claim 3 wherein the predetermined delta osmotic pressure level is a level no greater than 20 percent greater than the determined initial osmotic pressure.

6. A method for preventing hypotension as in claim 1 wherein the osmotic pressure setting is selected by an operator.

7. A method for preventing hypotension as in claim 1 wherein the osmotic pressure is determined across the permeable membrane of a filter used for fluid removal in the extracorporeal blood circuit.

8. A method for preventing hypotension as in claim 1 wherein the osmotic pressure is determined across the permeable membrane that is part of an ultrafiltration filter the extracorporeal blood circuit.

9. A method for preventing hypotension as in claim 1 wherein the osmotic pressure is determined after filtration through the permeable membrane is temporarily stopped followed shortly by temporarily stopping the blood flow.

10. A method for preventing hypotension as in claim 1 wherein the osmotic pressure is monitored while blood flow through the circuit is temporarily stopped.

11. A method for preventing hypotension as in claim 10 wherein the osmotic pressure is monitored during a temporary cessation of the removal of fluids from blood flowing through the blood circuit.

12. A method for preventing hypotension as in claim 10 wherein the osmotic pressure is periodically monitored during a temporary cessation in the blood flow and a temporary cessation of the removal of fluid, wherein the fluid is removal is ceased prior to ceasing the flood flow.

13. A method of controlling an extracorporeal blood circuit comprising:
   a. continuously withdrawing blood from a withdrawal blood vessel in a patient into the extracorporeal circuit;
   b. filtering fluids from blood flowing continuously through the circuit at a controlled filtration rate and using a filter;
   c. measuring osmotic pressure across the filter while the blood flow is temporarily stopped in the filter;
   d. reducing a filtration flow rate if the measured osmotic pressure exceeds a threshold osmotic pressure level.

14. A method of controlling an extracorporeal blood circuit as in claim 13 wherein the osmotic pressure is measured while the filtration rate is temporarily ceased through a filter performing said filtering.

15. A method of controlling an extracorporeal blood circuit as in claim 13 wherein the osmotic pressure is measured while blood flow through a filter and removal of fluids from the blood are temporarily ceased, and the removal of fluids is ceased before ceasing the blood flow.

16. A method of controlling an extracorporeal blood circuit as in claim 13 wherein the osmotic pressure is measured in a section of the circuit in which blood flow has been temporarily stopped for a period of ten seconds or less.

17. A method of controlling an extracorporeal blood circuit as in claim 16 wherein the filter is isolated from a section of the circuit withdrawing blood from the patient while the blood flow is temporarily stopped through the filter.

18. A system for treating blood from a patient comprising:
an extracorporeal circuit having a blood passage including a blood withdrawal tube, an osmotic pressure measurement device, a filter and an infusion tube,
said osmotic pressure measurement device includes a blood chamber in fluid communication with the blood passage, a filtrate chamber, and a permeable membrane separating the blood chamber and the filtrate chamber, wherein the membrane is impermeable to protein and blood cells and the filtrate chamber is filled with a fluid;
said filter having filter blood passage in fluid communication with the withdrawal tube, a blood outlet in fluid communication with the infusion tube, a filter membrane in fluid communication with the blood passage, a filter output section on a side of the membrane opposite to the blood passage, and a filtrate output line in fluid communication with the filter output section;
a pressure sensor sensing an osmotic pressure based on a pressure difference between blood in the blood chamber and filtrate in said filtrate chamber of the osmotic pressure measurement device, and said pressure sensor generating a pressure signal indicative of the osmotic pressure in the osmotic pressure measurement device;
a filtrate pump coupled to the filtrate output line and adapted to draw filtrate fluid from the filter at a controlled filtration rate, and
a filtrate pump controller regulating the controlled filtration rate based on the osmotic pressure.

19. A system as in claim 18 wherein the filtrate pump controller includes a processor and a memory storing a control algorithm to determine whether an osmotic pressure threshold is exceeded by the osmotic pressure determined from the pressure signal, said controller reducing the controlled filtration if the osmotic pressure exceeds the osmotic pressure threshold.

20. A system as in claim 18 wherein the osmotic pressure threshold is a set by an operator prior to treating blood.

21. A system as in claim 18 wherein the osmotic pressure threshold is determined based on a sum of an osmotic pressure level obtained during an initial phase of a treatment of the patient and a predetermined osmotic pressure difference.

22. A system as in claim 18 wherein the filter is a hemofilter.

23. A system as in claim 18 wherein the treatment device is a dialysis filter.

24. A system as in claim 18 wherein the treatment device is an ultrafiltration filter.

25. A system as in claim 18 wherein the pressure sensor comprises a pressure sensor in the blood withdrawal or return tube and a pressure sensor in the filtrate line.

26. A system as in claim 18 wherein the differential pressure sensor outputs a signal indicative of a pressure difference between the blood chamber of the osmotic pressure device and a portion of the blood passage coupled to the blood chamber.

27. A system as in claim 18 wherein the membrane in the osmotic pressure device is permeable to electrolytes in blood flowing through the blood chamber.

28. A system as in claim 18 wherein the differential pressure sensor operates.

* * * * *